United States Patent [19]

Walker et al.

[11] Patent Number: 5,747,029
[45] Date of Patent: May 5, 1998

[54] CONTROL OF WEEDS WITH A FUNGAL PATHOGEN DERIVED FROM M. VERRUCARIA

[76] Inventors: Harrell L. Walker, 1171 Highway 3072, Ruston, La. 71270; Anthony M. Tilley, 2567 Doc Steed Rd., Minden, La. 71055

[21] Appl. No.: 512,093

[22] Filed: Aug. 7, 1995

[51] Int. Cl.$^6$ .................................................. A01N 63/00
[52] U.S. Cl. .................. 424/93.5; 424/93.3; 435/254.1; 435/911
[58] Field of Search ................... 435/254.1, 911; 424/93.5, 93.3

[56] References Cited

U.S. PATENT DOCUMENTS

| | | | |
|---|---|---|---|
| 4,390,360 | 6/1983 | Walker | 71/79 |
| 4,419,120 | 12/1983 | Walker | 71/79 |
| 4,636,386 | 1/1987 | Anderson et al. | 424/93 |
| 4,643,756 | 2/1987 | Cardina et al. | 71/79 |
| 4,755,207 | 7/1988 | Bannon | 71/79 |
| 4,767,441 | 8/1988 | Walker et al. | 71/79 |
| 4,776,873 | 10/1988 | Caulder et al. | 71/79 |
| 4,808,207 | 2/1989 | Gotlieb et al. | 71/73 |
| 4,871,386 | 10/1989 | Riley | 71/79 |
| 4,902,333 | 2/1990 | Quimby, Jr. | 71/79 |
| 5,074,902 | 12/1991 | Connick, Jr. et al. | 71/79 |
| 5,314,691 | 5/1994 | Coffey et al. | 424/93 Q |

OTHER PUBLICATIONS

Phytopathology, vol. 84:10, 1994 pp. 1136–1137, Control of Carduus Acanthoides With *Myrothecium Verrucaria* in the Greenhouse In the Absence of Dew Yang. Abstract #562.

Detrich IBG News, May 1995, vol. 4, No. 1, pp. 7–8 "Classical Biological Control of Weeds With Pathogens".

Plant Diseases Oct., 1995, vol. 79 No. 10 pp. 994–997, Host Range Determination of *Myrothecium Verrucaria* from Leafy Spurge–Yang et al.

Plant Diseases Oct., 1995, vol. 79 No. 10, pp. 998–1002 Factors Influencing Pathogenicity of *Myrothecium Verrucaria* Isolated From *Euphorbia escla* on Species of Euphorbia–Yang et al.

*Primary Examiner*—Chhaya D. Sayala
*Attorney, Agent, or Firm*—John M. Harrison; Randall C. Brown; Rick Matos

[57] ABSTRACT

A method for the biological control of various weeds such as sicklepod using the fungus *Myrothecium verrucaria*. In a typical application, conidia of the fungus are applied with liquid surfactant to the weeds in amounts effective to produce typical plant lesions which kill or suppress, and thus control, the weeds. In another embodiment, phytotoxin produced by the fungus is used to control the weeds. In still another embodiment a synergistic combination of *M. verrucaria* and the fungus *Alternaria cassiae* is used to control sicklepod and in a fourth embodiment phytotoxin produced by *M. verrucaria* is used synergistically with *A. cassiae* to control sicklepod. A strain of *M. verrucaria* is on deposit with the Department of Biological Sciences, Louisiana Tech University in Ruston, La. and with the patent collection of the International Mycological Institute in Surrey, UK and has been assigned the number IMI 368023.

11 Claims, 4 Drawing Sheets

CONTROL OF WEEDS WITH A FUNGAL PATHOGEN DERIVED FROM M. VERRUCARIA

BACKGROUND OF THE INVENTION

1. Field of the Invention

This invention relates to bioherbicides for controlling pest plants such as weeds and more particularly, to a method for the biological control of a variety of pest plants, including sicklepod, using the fungus *Myrothecium verrucaria*. Typically, in a first embodiment a selected concentration of conidia in a mixture of distilled water and liquid surfactant such as SILWET L-77 (trademark), is applied to the pest plants to produce typical lesions which kill or suppress, and thus control, the plants. In a second embodiment, phytotoxin is rinsed from the conidia by subjecting the conidia to sequential centrifugation cycles, and applied to the plants using distilled water or a mixture of distilled water and a surfactant. In a third embodiment, a synergistic combination of *M. verrucaria* and the fungus *Alternaria cassiae* in a mixture of distilled water and surfactant is applied to the plants to achieve enhanced control of the plants, and in a fourth embodiment, phytotoxin extracted from *M. verrucaria* is used in combination with *Alternaria cassiae* in a mixture of distilled water and surfactant to synergistically control the pest plants.

Weeds present a tremendous problem to farmers throughout the world, causing an estimated 10–12% loss of value for agricultural products in the United States, the most recent estimate being $20 billion annually, according to McWhorter, C. G. [1984] Weed Science, 32:850–855. Chemical pesticides are commonly used to control weeds in agricultural crops, but concern over environmental damage caused by these pesticides has recently elicited societal pressures to replace the chemical pesticides with alternative control methods. One area of active research in this area involves the use of plant pathogens, including both bacteria and fungi, to attack and kill pest plants in agricultural crops.

A major constraint to commercial development of a plant pathogen as a biological herbicide can be selectivity. A pathogen that controls only one weed species in one type of crop does not have the same market potential as a pathogen that controls several important weed species in different types of crops. It has surprisingly been found that the fungus *Myrothecium verrucaria* is effective in controlling multiple varieties of weeds in several different types of important agricultural crops. In addition to controlling sicklepod, the *M. verrucaria* utilized in this invention is effective in controlling pigweed, spurred anoda, jimsonweed, hemp sesbania, and other susceptible weeds, but does not harm Bermudagrass and Centipedegrass and therefore may also be used to control weed growth in some residential and commercial lawns and turf. It has also surprisingly been found that conidia of *M. verrucaria* or phytotoxin produced by *M. verrucaria* may be applied to the weeds in combination with conidia of the fungus *Alternaria cassiae*, to enhance the pathogenic action of *A. cassiae* on sicklepod.

2. Description of the Prior Art

Several methods are known in the art for using microorganisms to control weeds and other pest plants. As disclosed in U.S. Pat. No. 3,999,973, to Daniel, et al. the anthracnose fungus *Colletotrichum gloeosporioides* has been used to control the weed northern jointvetch and another strain of this fungus has been used to control winged waterprimrose. *Colletotrichum malvarum* has been used to control prickly sida. These three pathogens have been combined to control all three target weeds at once. In other experimental work the fungus *Alternaria macrospora* has been used to control spurred anoda (*Anoda cristata*), Weed Science, H. L. Walker, 1981, Vol. 29, pp. 505–507.

Research activity involving *Myrothecium verrucaria* is noted on page 8 of the IBG News, May, 1995 issue, Vol. 4 No. 1. My U.S. Pat. No. 4,390,360, dated Jun. 28, 1983, describes "Control of Sicklepod, Showy Crotalaria and Coffee Senna With A Fungal Pathogen" using a specific host strain of the fungus *Alternaria cassiae* to produce typical weed lesions which kill or suppress the respective weeds. My U.S. Pat. No. 4,419,120, dated Dec. 6, 1983, discloses "Control of Prickly Sida, Velvetleaf and Spurred Anoda With Fungal Pathogens" using a specific host strain of the fungus *Fusarium lateritium* to kill or suppress the respective weeds. U.S. Pat. No. 4,715,881, dated Dec. 29, 1987, to Andersen, et al., details "Control of Eastern Black Nightshade With a Fungal Pathogen" using a strain of *Colletotrichum coccodes* which is pathogenic toward eastern black nightshade (*Solanum ptycanthum*). My U.S. Pat. No. 4,718,935, dated Jan. 12, 1988 and U.S. Pat. No. 4,767,441, dated Aug. 30, 1988, describe a "Method For The Preparation of Mycoherbicide-Containing Pellets" characterized by alginate gel pellets containing living fungus capable of producing conidia when exposed to sufficient light and moisture. U.S. Pat. No. 4,724,147, dated Feb. 9, 1988, to James J. Marois, et al. and U.S. Pat. No. 4,818,530, dated Apr. 4, 1989, also to James J. Marois, et al. both detail the "Preparation of Pellets Containing Fungi for Control of Soilborne Diseases", in which fungi are first selected and grown for a time sufficient to produce inoculum. The fungal propagules are harvested, homogenized and diluted with sodium alginate solution. Pelletization is then accomplished by dropwise addition of the fungal propagule-alginate mixture into a solution of calcium chloride or calcium gluconate. The resulting alginate gel pellets containing living fungi can then be dried and used to inoculate agricultural fields infested with soilborne plant diseases. U.S. Pat. No. 5,192,541, dated Mar. 9, 1993, to Steven D. Savage, et al. describes "Weed-Killing *Xanthomonas campestris*", in which novel microorganisms useful in controlling unwanted grasses and other weeds are discovered through a unique process which involves isolating plant pathogens from asymptomatic plants. U.S. Pat. No. 5,393,728, dated Feb. 28, 1995, to Charudattan, et al. details a "Broad Spectrum Bioherbicide to Control Several Species of Pigweeds", in which a novel *Phomopsis* sp. fungus is used as an effective broad-spectrum bioherbicide for controlling pigweed.

The prior art teaches that fungi developed as biological herbicides should be restricted in host range to one or a limited number of closely related plant species. *M. verrucaria*, when manipulated as described, exhibits herbicidal activity for a much wider range of plant species in numerous plant families than has been previously reported.

Previous research has shown that not all plant pathogens are suitable candidates for manipulation as biological herbicides. Indeed, of the hundreds of fungi studied as potential biological herbicides, only a very small number have been developed as biological herbicides. There are no previous reports of any attempts to use any *Myrothecium* species as biological herbicides. *M. verrucaria* under ordinary circumstances is only weakly pathogenic. The process that we developed to manipulate this fungus provides for a dramatic increase in pathogenic activity and increases the host range to include many plant species not previously reported to be hosts for the fungus. The host range of this fungus could not have been predicted.

Pathogenic activity is enhanced by unusually high numbers of spores that are applied in a suitable surfactant. As the research results herein indicate, large numbers of spores applied in water only, will not produce the desired level of disease activity. The type of surfactant also influences disease activity. The use of nonoxynol (9 to 10 POE) [a-(p-nonylphenyl)-w-hydroxypoly (oxyethylene)] surfactant, marketed as STEROX N.J. (trademark) and the organosilicone surfactant SILWET L-77 (trademark) results in significant increases in disease activity. Inoculum concentration has been shown to be important in the performance of potential biological herbicides, but the dramatic increases in disease activity with increased inoculum levels could not have been predicted. Prior art also teaches that surfactant selection can provide increased levels of activity, but the dramatic increases in disease activity and host range documented herein for this fungus could not have been predicted based on prior art.

The responses of closely related species of plants can vary greatly from no symptoms for some species to severe stunting or death for other species. These differential responses of closely related species could not have been predicted. Combinations of *A. cassiae* and *M. verrucaria* exhibited synergistic activity that could not have been predicted. Many organisms used in combination exhibit antagonistic activity toward each other, resulting in lower levels of control than would be expected from either pathogen alone. Results indicating that combinations of *A. cassiae* and *M. verrucaria* are synergistic could not have been predicted. This is especially true in view of our observations and reports by others that *M. verrucaria* inhibits the growth in vitro of a number of fungi, including Alternaria spp.

The selectivity that can be obtained by the method of application could not have been predicted based on prior art. Test results indicate the potential for using directed spray applications to control susceptible weed species growing beneath crop canopies. When spores plus certain surfactants are applied over the top of the foliage of some important crop species, such as soybeans or cotton, many of the plants are killed, as tabulated in Table I, herein. However, it was observed that when the same spore suspensions are applied below the leaves, these crop species were not adversely affected.

*Myrothecium verrucaria* is cosmopolitan and there are numerous reports in the literature related to this species. This organism is usually considered to be a soil inhabiting organism that is nonpathogenic or weakly pathogenic. No reports of disease injury caused by this organism document results that would suggest possible use of *M. verrucaria* as a microbial herbicide.

The invention set forth in this application is based on a combination of factors that include the particular isolate of *M. verrucaria*, inoculum concentration, and the use of a suitable surfactant. The dramatic interactions that the test data indicate could not have been predicted from the prior art.

Effective inoculum concentrations, when applied in water only, result in levels of efficacy that are too low for use as a biological herbicide.

No other potential microbial herbicide reported in the scientific literature maintained herbicidal activity at 35° C. with no apparent reduction in efficacy. Indeed, the herbicidal activity of this invention appeared to increase with temperature, as indicated by the number of plants that exhibited collapse of stem and leaf tissue immediately following a 6 hour dew period at 35° C.

Prior art teaches that fungi applied as microbial herbicides to the foliage of target plants require dew periods, typically 6 to 18 hours, for desired efficacy. There are numerous reports of special formulations involving invert emulsions, oils, or hydrophilic ingredients to circumvent or supplement requirements for moisture. Our invention provides a control which is not dependent upon these formulations.

SUMMARY OF THE INVENTION

The present invention is directed to a method for biological control of various weeds, including sicklepod, pigweed, spurred anoda, jimsonweed, hemp sesbania, and other susceptible weeds using the fungus *Myrothecium verrucaria*. The fungus is initially isolated from diseased plants and then conidia are produced during incubation in petri dish cultures. In one embodiment inoculum is produced by harvesting conidia from the petri dishes using distilled water or a surfactant in distilled water. In another embodiment the harvested conidia are rinsed in distilled water through repeated cycles of centrifugation. Resulting cell-free filtrates containing phytotoxin rinsed from the fungus are applied to the weeds, either alone or in combination with conidia of the fungus *Alternaria cassiae*, to enhance pathogenic action of the fungus. In still another embodiment inoculum is produced by combining conidia of *M. verrucaria* and those of *A. cassiae* in a surfactant, to synergistically enhance pathogenic action of *A. cassiae*.

BRIEF DESCRIPTION OF THE DRAWINGS

The invention will be better understood by reference to the following drawings, wherein.

DESCRIPTION OF THE PREFERRED EMBODIMENTS

*Myrothecium verrucaria* (Alb. and Schwein) Ditmar ex Fr. is on deposit with the Department of Biological Sciences, Louisiana Tech University in Ruston, La. and was placed on deposit with the International Mycological Institute, Bakeham Lane, Egham Surrey, UK on May 18, 1994, as IMI number 361690. The deposit was placed in the patent collection of the International Mycological Institute and has been assigned the accession number IMI 368023. The date of deposit was Jun. 21, 1995. The address of the Department of Biological Sciences is: Louisiana Tech University, Harrell L. Walker, Department of Biological Sciences, P.O. Box 3179, TS., Ruston, La. 71272.

According to (Tulloch, M. 1972, The Genus Myrothecium Tode ex Fr. Mycological Papers 130:1–42), *M. verrucaria* is described as follows: "Spore mass wet, black, convex surrounded by wet floccose margin. Spores broadly fusiform, one end pointed the other protruding and truncate, in erythrosin and NH4 solution with a fantailed appendage on the pointed end, 6.5–8×2.3–5 microns."

The *Myrothecium verrucaria* used in this invention was isolated from diseased plants of sicklepod, a new host record for this fungus. Unless otherwise stated, the fungus was cultured on potato dextrose agar (PDA) in petri dishes that were inverted and placed on open-mesh, wire shelves of a Percival model I 35 LLVL incubator at 24° C. Twelve-hour photoperiods were provided by two, 20-watt cool-white fluorescent lights directed upwardly from 10 cm. below the cultures. Colonies produced concentric rings of spores (conidia) under these culture conditions and the spores were harvested by rinsing the cultures with 0.05% surfactant. Inoculum was prepared by suspending the conidia in 0.05% surfactant and adjusted to a concentration of $20 \times 10^6$ conidia per ml, using a hemacytometer.

Unless otherwise indicated, experimental units consisted of groups of 12 plants that were grown in peat strips of 12, 5.8 cm square pots. The growing medium consisted of a commercial blend of peat and perlite that was supplemented with controlled release 13— 13—13 fertilizer. Plants were sprayed to wetness with foliar applications of spore suspensions containing $20 \times 10^6$ conidia per ml and 0.05% (v/v) SILWET L-77 (trademark), a silicone-polyether copolymer spray adjuvant. Control groups were sprayed with 0.05% surfactant only. Aerosol sprayers were used to make the applications and treatments were replicated three times.

Conidia of *M. verrucaria* were harvested from cultures grown on PDA and rinsed three times in distilled water by sequential centrifugation cycles at 840× g for 10 minutes per cycle. A cell-free filtrate was prepared by filtering the supernatant from the first centrifugation cycle through 0.2 micron membrane filters. The washed conidia produced only mild disease symptoms when inoculated to host plants, indicating an important role of phytotoxin in disease development. The cell-free filtrate containing phytotoxin resulted in a decrease in dry weight, but minimum rates of mortality, when applied to sicklepod.

Conidia of *M. verrucaria* and conidia of *A. cassiae* were harvested from cultures grown on PDA and vegetable juice agar, respectively, suspended in 0.05% surfactant, to a concentration of $5 \times 10^4$ *A. cassiae* conidia per ml and $1 \times 10^7$ *M. verrucaria* conidia per ml. The mixture was subsequently applied to test plants. Combinations of *A. cassiae* and *M. verrucaria* surprisingly exhibited a synergistic effect on the test plants, resulting in a considerably greater kill rate of the plants than was achieved using either fungus alone.

Conidia of *M. verrucaria* were harvested from cultures grown on PDA and rinsed once in distilled water by a centrifugation cycle at 840× g for 10 minutes. The *M. verrucaria* conidia were discarded and a cell-free filtrate was prepared by filtering the supernatant through 0.2 micron membrane filters. *Alternaria cassiae* conidia were suspended in the cell-free filtrate, which was subsequently applied to test plants. Combinations of *A. cassiae* and cell-free filtrate derived from *M. verrucaria* conidia surprisingly exhibited a synergistic effect on the test plants, resulting in a considerably greater kill rate of the plants than was achieved using either *A. cassiae* or cell-free filtrate alone.

A number of plant species, representing a number of different families, were tested for reaction to foliar applications of the fungus and the results were tabulated in Table I. Test plants in the cotyledon to second leaf stage of growth were inoculated and placed in unlighted dew chambers for six hours at 25° C., then moved to greenhouse benches and observed for disease development. Results indicate that *M. verrucaria*, when manipulated according to the method of the invention, has a broad host range that includes plant species in a number of families. A search of the literature indicated that many of these species apparently are new hosts for *M. verrucaria*, and these species are also indicated in Table I. It was surprisingly found that most of the grasses and sedges tested were much more tolerant of the fungal preparation than were most of the broadleaved species tested. Among the broadleaved species, unexpected differences in susceptibilities were found. For example, sicklepod was highly susceptible to the fungus, while coffee senna, a closely-related species in the same genus, was much more tolerant. Velvetleaf was highly susceptible, yet prickly sida, a species in the same family, was much more tolerant. The data presented in Table I document these and other examples of differences in responses by closely-related species.

TABLE 1

| HOST RANGE RESPONSE TO *MYROTHECIUM VERRUCARIA* | | | | | |
|---|---|---|---|---|---|
| FAMILY SCIENTIFIC NAME | COMMON NAME | MORTALITY (%) 7 DAYS | MORTALITY (%) 14 DAYS | DRY WEIGHT REDUCTION (%) | NEW HOST RECORD |
| AMARANTHACEAE | | | | | |
| *Amaranthus retroflexus* L. | Pigweed, redroot | 78 | 81 | 89 | YES |
| CHENOPODIACEAE | | | | | |
| *Beta vulgaris* L. | Beet 'Detroit Dark Red' | 100 | 100 | 94 | YES |
| *Chenopodium amaranticolor* Coste & Reynier | Chenopodium | 89 | 92 | 90 | YES |
| COMPOSITAE | | | | | |
| *Tagetes sp.* | Marigold 'Petite Yellow' | 6 | 8 | 80 | YES |
| *Helianthus annuus* L. | Sunflower 'Mammoth Gray Stripe' | 42 | 83 | 86 | YES |
| [1]*Xanthium pensylvanicum* Wallr. | Cocklebur | 0 | 17 | 91 | |

TABLE 1-continued

HOST RANGE RESPONSE TO *MYROTHECIUM VERRUCARIA*

| FAMILY SCIENTIFIC NAME | COMMON NAME | MORTALITY (%) 7 DAYS | MORTALITY (%) 14 DAYS | DRY WEIGHT REDUCTION (%) | NEW HOST RECORD |
|---|---|---|---|---|---|
| *Zinnia elegans* Jacq. | Zinnia 'Sombrero' | 14 | 75 | 90 | YES |
| CONVOLVULACEAE | | | | | |
| *Ipomea spp.* | morning glory | 0 | 0 | 35 | |
| CRUCIFEREAE | | | | | |
| *Brassica rapa* L. | Turnip 'Seven Top' | 33 | 47 | 83 | YES |
| *Raphanus sativus* L. | Radish 'Cherry Belle' | 100 | 100 | 93 | YES |
| CUCURBITACEAE | | | | | |
| *Cucumis melo* L. | Cantaloupe 'Hale's Best Jumbo' | 0 | 0 | 73 | |
| *Cucumis sativus* L. | Cucumber 'Straight 8' | 19 | 22 | 54 | |
| *Curcubita pepo* L. | Pumpkin 'Jack-O'-Lantern' | 25 | 33 | 70 | |
| *Cucurbita pepo* var. *melopepo* (L.) Alef. | Squash 'Yellow Crookneck' | 0 | 0 | 43 | |
| *Citrullus vulgaris* Schrad. | Watermelon 'Charleston Gray' | 0 | 0 | 49 | |
| CYPERACEAE | | | | | |
| [2]*Cyperus rotundus* L. | Nutsedge, purple | 0 | 0 | 0 | |
| GRAMINEAE | | | | | |
| [3]*Brachiaria platyphylla* (Griseb.) Nash | Signalgrass, broadleaf | 0 | 0 | 7 | |
| [4]*Cynodon dactylon* (L.) Pers. | Bermudagrass 'Tifway 328' | 0 | 0 | 30 | |
| [3]*Digitaria ciliaris* (Retz.) Koel. | Crabgrass, southern | 0 | 0 | 14 | |
| [3]*Echinochloa crus-galli* (L.) Beauv. | Barnyardgrass | 0 | 0 | 20 | |
| [4]*Eremochloa ophiuroides* (Munro) Hack. | Centipedegrass | 0 | 0 | 22 | |
| [3]*Leptochloa* sp. | Sprangletop, tighthead | 0 | 0 | 60 | |
| [3]*Poa annua* L. | Bluegrass, annual | 0 | 0 | 26 | |
| [3]*Setaria viridis* (L.) Beauv. | Foxtail, green | 0 | 0 | 28 | |
| *Sorghum bicolor* (L.) Moench | Sorghum, grain 'Delta Pine G522DR' | 0 | 0 | 4 | |
| [3]*Sorghum halepense* (L.) Pers. | Johnsongrass | 0 | 0 | 45 | |
| [4]*Stenotaphrum secondatum* (Walt) Ktze. | St. Augustinegrass | 0 | 0 | 0 | |
| *Zea mays* L. | Corn 'Trucker's Favorite' | 0 | 0 | 0 | |
| [4]*Zoysia* sp. | Zoysiagrass | 0 | 0 | 1 | |
| LEGUMINOSAE | | | | | |
| *Arachis hypogoea* L. | Peanut 'Improved Spanish' | 0 | 0 | 15 | |
| *Cassia obtusifolia* L. | Sicklepod | 97 | 97 | 96 | YES |
| *Cassia occidentalis* L. | Senna, coffee | 0 | 0 | 50 | YES |
| *Glycine max* (L.) Merr. | Soybean | | | | |
| | 'Braxton' | 0 | 0 | 67 | |
| | 'Cajun' | 0 | 0 | 65 | |
| | 'Crawford' | 0 | 0 | 66 | |
| | 'Forrest' | 0 | 0 | 75 | |
| *Phaseolus vulgaris* L. | Bean, garden | | | | |
| | 'Kentucky Wonder' | 0 | 0 | 79 | |
| | 'Henderson Bush' | 0 | 0 | 76 | |
| *Pisum sativum* L. | Pea, English 'Early Alaskan' | 56 | 89 | 72 | |
| *Sesbania exaltata* (Raf.) Cory | Sesbania, hemp | 100 | 100 | 90 | YES |
| *Vigna sinensis* (Torner) Savi. | Cowpea 'California Pinkeye Purple Hull' | 0 | 0 | 87 | YES |
| MALVACEAE | | | | | |
| *Abelmoschus esculentus* | Okra | 0 | 0 | 53 | |

TABLE 1-continued

HOST RANGE RESPONSE TO *MYROTHECIUM VERRUCARIA*

| FAMILY SCIENTIFIC NAME | COMMON NAME | MORTALITY (%) 7 DAYS | MORTALITY (%) 14 DAYS | DRY WEIGHT REDUCTION (%) | NEW HOST RECORD |
|---|---|---|---|---|---|
| (L.) Moench | 'Clemson Spineless' | | | | |
| *Abutilon theophrasti* Medic. | Velvetleaf | 0 | 9 | 55 | YES |
| *Anoda cristata* (L.) Schlecht. | Anoda, spurred | 64 | 69 | 90 | YES |
| *Gossypium hirsutum* L. | Cotton | | | | |
| | 'Stoneville 453' | 0 | 0 | 84 | |
| | 'Stoneville 506' | 0 | 0 | 81 | |
| *Sida spinosa* L. | Sida, prickly | 0 | 0 | 53 | YES |
| SOLANACEAE | | | | | |
| *Capsicum frutescens* L. | Pepper, green 'California Wonder' | 0 | 0 | 0 | |
| *Datura stramonium* L. | Jimsonweed | 100 | 100 | 97 | YES |
| *Lycopersicon esculentum* Mill. | Tomato 'Marglobe' | 0 | 0 | 26 | |
| *Solanum ptycanthum* Dun. | Nightshade, eastern black | 0 | 0 | 37 | |
| [5]*Solanum tuberosum* L. | Potato | | | | |
| | 'Kennebec' | 0 | 0 | 16 | |
| | 'Krantz' | 0 | 0 | 31 | |
| | 'Red LaSoda' | 0 | 0 | 3 | |

[1]Grown from seed, one plant per 7.6 cm pot. Each replication consisted of plants in four pots.
[2]Grown from field plants, 2–4 plants per 7.6 cm pot, and each replication consisted of plants in one pot.
[3]Seeds were broadcast in 5.7 cm peat pots, twelve pots per strip. Plants were thinned to 5–10 seedlings per pot.
[4]Centipedegrass, bermudagrass, St. Augustinegrass, and zoysiagrass were grown in 7.6 cm pots, and each replication consisted of plants in one pot.
[5]Grown from tubers, two plants per 15.2 cm pot, and each replication consisted of plants in one pot.

The following examples illustrate application of the fungus *Myrothecium verrucaria* in controlling weeds:

EXAMPLE 1

Figure 1:
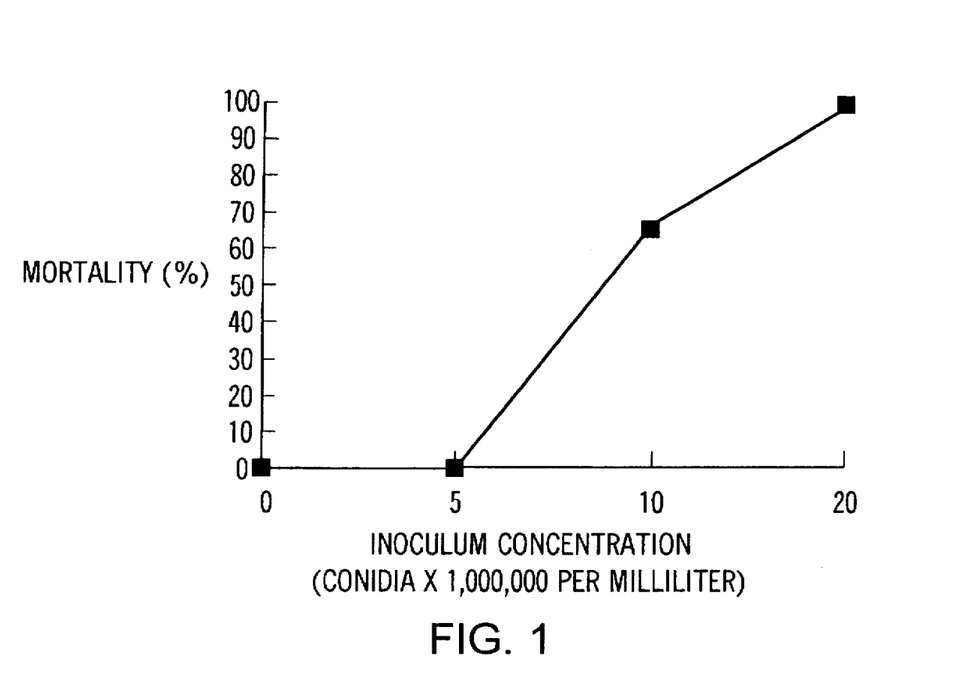
FIG. 1 is a graph of *Myrothecium verrucaria* inoculum concentration (conidia) vs. mortality (%) of sicklepod.

Effect of Inoculum Concentration on Mortality of Sicklepod Seedlings:

Sicklepod seedlings were inoculated with suspensions containing 0, 5, 10, or $20 \times 10^6$ conidia per ml and surfactant according to the procedure outlined above. The most effective inoculum concentration for control of sicklepod under these conditions was in the range of $20 \times 10^6$ conidia per ml, as illustrated in FIG. 1.

EXAMPLE 2

Figure 2:
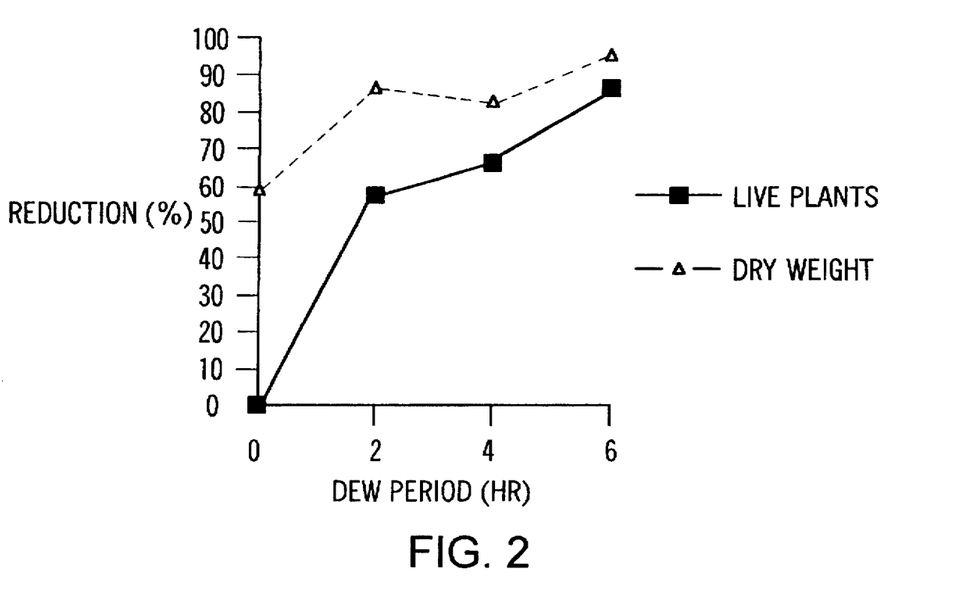
FIG. 2 is a graph of dew period (hr) vs. reduction (%) of sicklepod by *Myrothecium verrucaria*.

Effect of Dew Duration on Dry Weight and Mortality of Sicklepod Seedlings:

Sicklepod seedlings were inoculated and placed in dew chambers as described in the above-delineated procedure. After 0, 4, and 6 hours, inoculated and control plants were removed from the dew chambers, placed on greenhouse benches, and observed for disease development. A dew period of 6 hours resulted in 85% kill of sicklepod seedlings 14 days after inoculation, as illustrated in FIG. 2. At an inoculum level of $20 \times 10^6$ spores per ml there was a 60% reduction in dry weight with no dew following inoculation.

EXAMPLE 3

Figure 3:
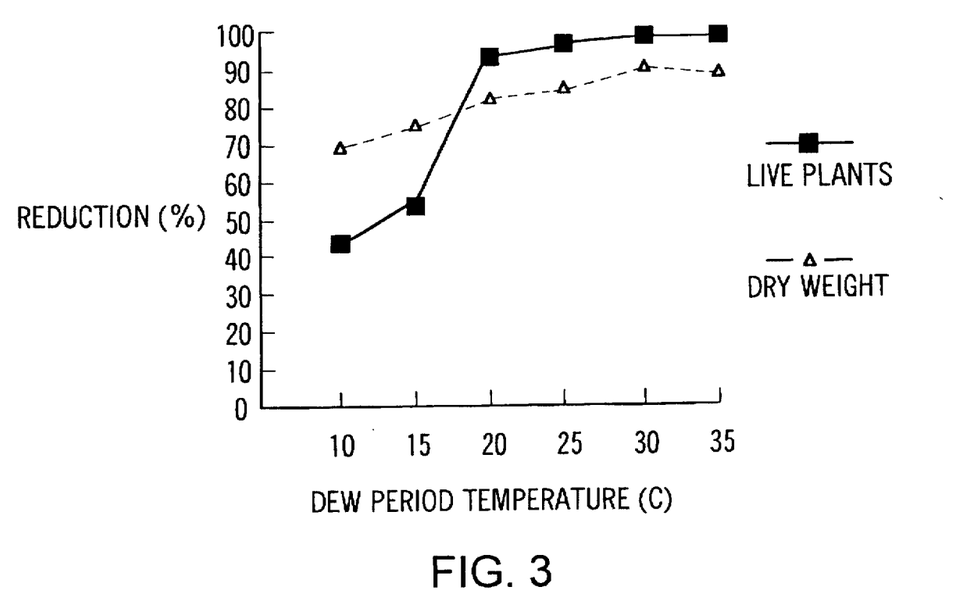
FIG. 3 is a graph of dew period temperature (° C.) vs. reduction (%) of sicklepod by *Myrothecium verrucaria*.

Effect of Dew Period Temperature on Dry Weight and Mortality of Sicklepod Seedlings:

Sicklepod seedlings were inoculated with $20 \times 10^6$ conidia per ml and placed in dew chambers at 10°, 15°, 20°, 25°, 30°, and 35° C. for 6 hours according to the procedure described above. Control plants were sprayed with surfactant only and were included for each temperature. Up to 100% kill of sicklepod seedlings was consistently observed with dew temperatures of 25° C. to 35° C., as illustrated in FIG. 3. The rate of expression of disease severity increased with temperature up to the maximum 35° C. tested. Collapse of leaf and stem tissue was often noted as inoculated plants were removed from the dew chambers following a 6 hour dew period at 35° C.

No other potential microbial herbicide ever reported in the scientific literature maintained herbicidal activity at 35° C. with no apparent reduction in efficacy. Indeed, the herbicidal activity of our invention appeared to increase with temperature, as indicated by the number of plants that exhibited collapse of stem and leaf tissue immediately following a 6 hour dew period at 35° C.

EXAMPLE 4

Figure 4A:
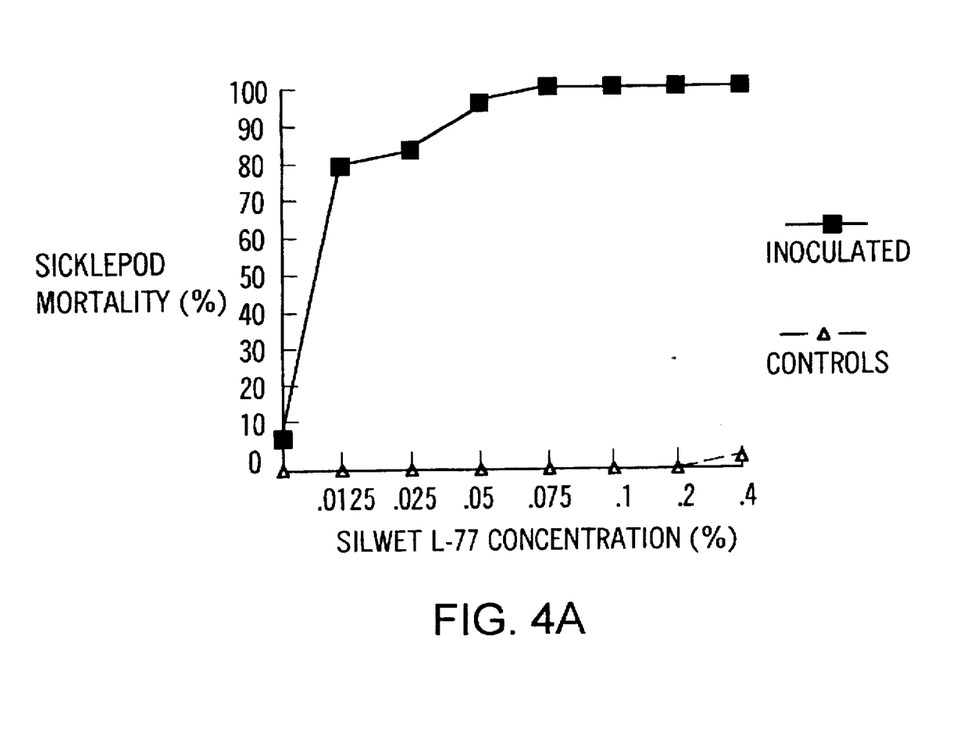
FIG. 4A is a graph of SILWET L-77 (trademark) surfactant concentration (%) on *Myrothecium verrucaria* vs. sicklepod mortality (%)

Effect of various concentrations of SILWET L-77 (trademark) on Mortality and Dry Weight of Sicklepod Seedlings The dramatic increase in mortality of sicklepod with the addition of SILWET L-77 (trademark) in increasing concentrations is illustrated in FIG. 4A. Maximum sicklepod kill was realized at a SILWET L-77 (trademark) concentration of 0.075%. Limited sicklepod mortality was noted in the SILWET L-77 (trademark) application as a control without the fungus at surfactant concentration of from 0.2 to about 0.4%.

Figure 4B:
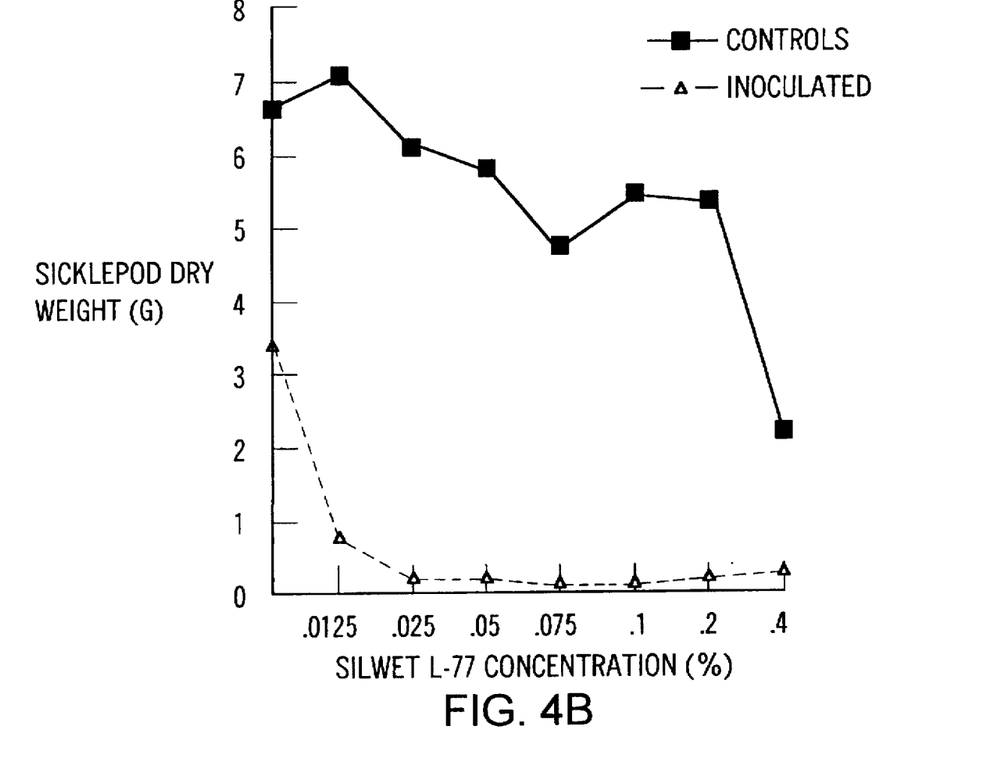
FIG. 4B is a graph of SILWET L-77 (trademark) surfactant concentration (%) vs. sicklepod dry weight (G)

FIG. 4B shows that under circumstances where the SILWET L-77 (trademark) concentration exceeds 0.2% to 0.4% of the surfactant only, without the fungus, as a control application, then there is a reduction in sicklepod dry weight.

EXAMPLE 5

Effect of Different Surfactants on Mortality of Sicklepod Seedlings:

Spore suspensions containing $20 \times 10^5$ conidia per ml were prepared in distilled water only, 0.05% (w/v) oxysorbic (20 POE) polyoxyethylene sorbitan mono oleate (TWEEN 80)

(trademark) surfactant, 0.02% (v/v) nonoxynol (9 to 10 POE) [α-(p-nonylphenyl)-ω-hydroxypoly (oxyethylene)] (STEROX NJ) (trademark) surfactant, and 0.05% (w/v) of SILWET L-77 (trademark), as heretofore described. Sicklepod seedlings were inoculated, placed in dew chambers at 25° C. for 6 hours and moved to greenhouse benches, as previously described. Control plants were sprayed with water or surfactant only.

Figure 5:
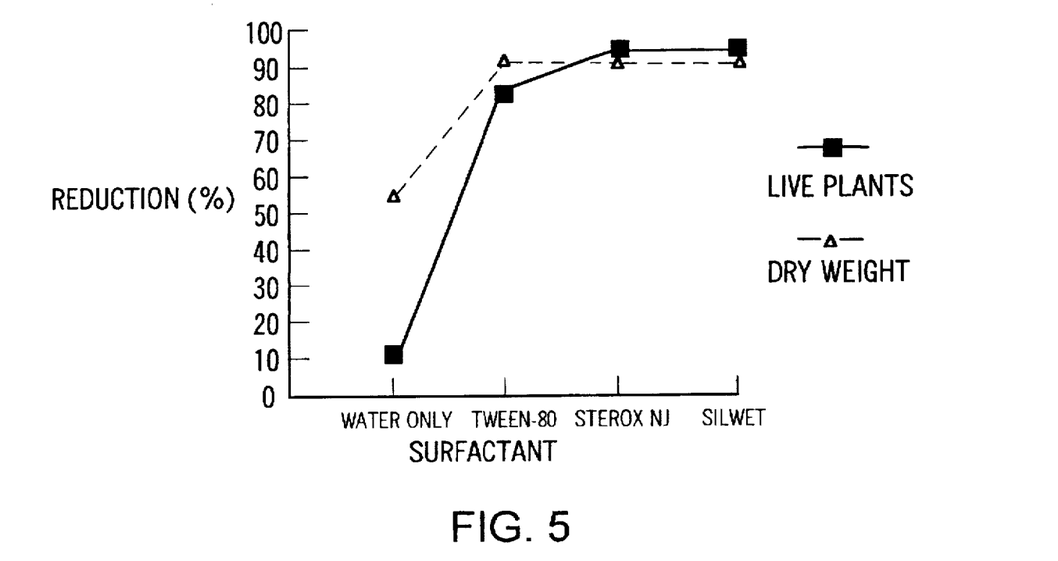
FIG. 5 is a graph of selected surfactants vs. reduction (%) of sicklepod.

Seedling mortality was recorded 14 days after inoculation, and these data are presented in FIG. 5. As indicated in FIG. 5, only 11% of the plants were killed when the spores were suspended in water only, whereas 94% of the plants were killed when the spores were suspended in SILWET L-77 (trademark) or STEROX NJ (trademark). The treatment utilizing the TWEEN 80 (trademark) surfactant was intermediate, resulting in 83% mortality.

Figure 6:
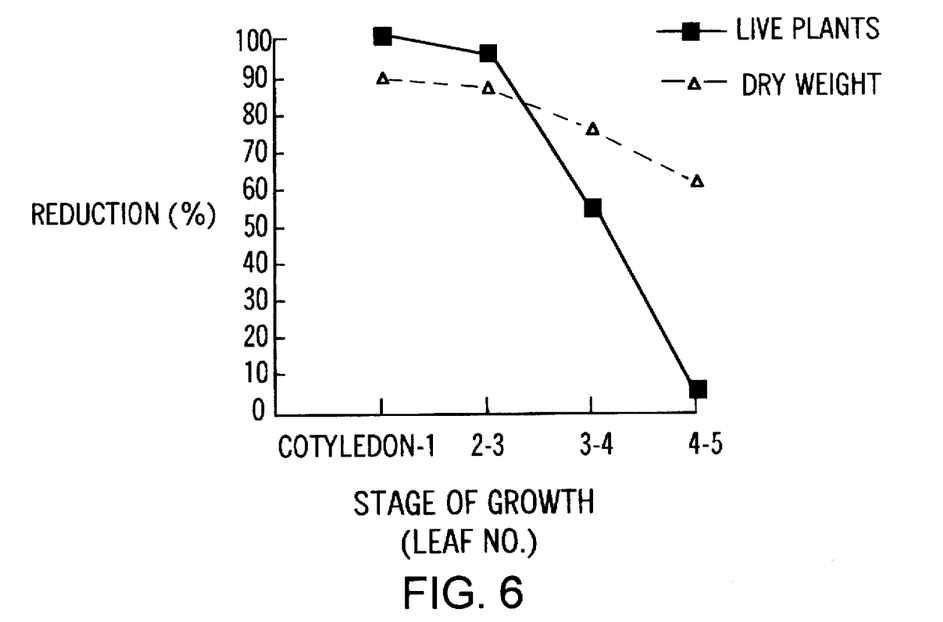
FIG. 6 is a graph of stage of growth (leaf no.) of sicklepod seedlings vs. reduction (%) of sicklepod.

EXAMPLE 6
Sicklepod Dry Weight and Mortality as Influenced by Stage of Growth of Sicklepod Plants at Time of Inoculation:

Sicklepod seedlings in the cotyledonary to sixth true-leaf stage of growth were inoculated, placed in dew chambers for 6 hours, then moved to greenhouse benches, as previously described. Data for dry weight and mortality 14 days after inoculation are presented in FIG. 6.

Figure 7:
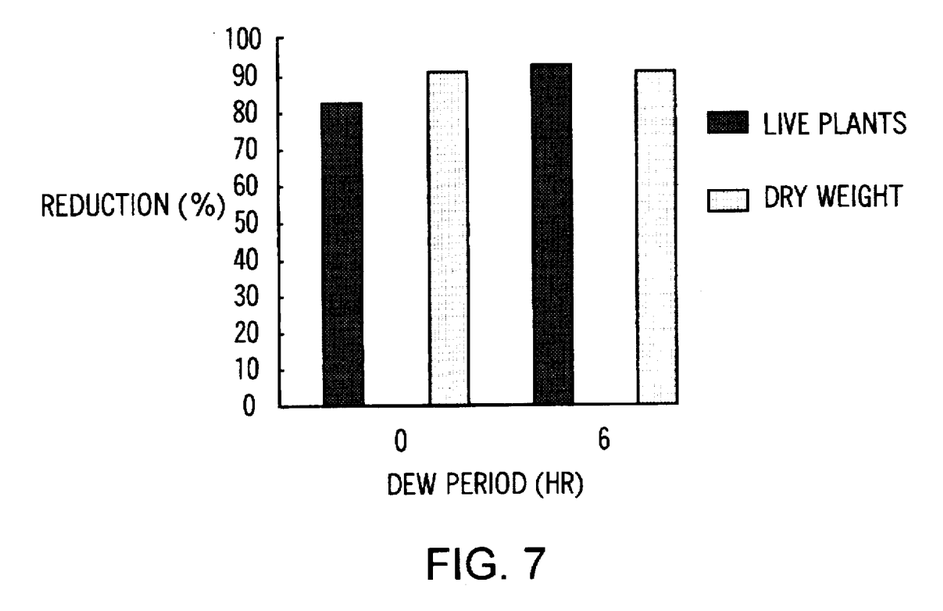
FIG. 7 is a bar graph of dew period (hr) vs. reduction (%) of sicklepod.

EXAMPLE 7
Increased Inoculum Levels Reduce the Dew Requirement:

As reported for many other pathogens, we observed an interaction of several variables, particularly spore concentration, length of dew period, growth stage of plants and surfactants. Other factors can also be important, but manipulation of each of these parameters can significantly affect results. For example, by extending the dew period from 6 hours to 18 hours, mortality of sicklepod plants can be increased with the same inoculum concentration. Also, by extending dew periods and increasing inoculum levels, larger sicklepod plants can be controlled. An inoculum level of $4 \times 10^7$ conidia per ml, suspended in 0.075% SILWET L-77 (trademark) resulted in significant mortality of sicklepod seedlings with no dew, as illustrated in FIG. 7.

EXAMPLE 8
Efficacy of *M. verrucaria* as Affected by Rinsing of Spores:

A number of reports indicate phytotoxicity associated with sporodochial fluids from petri dish cultures and metabolites produced in submerged liquid cultures. Conidia of *M. verrucaria* harvested from cultures grown on PDA as previously described, were rinsed three times in distilled water by sequential centrifugation cycles. These washed conidia that were rinsed using repeated cycles of centrifugation did not produce any mortality or dry weight reduction when inoculated to host plants, indicating an important role of phytotoxin in disease development. Cell-free filtrates containing phytotoxin when applied to sicklepod resulted in a decrease in dry weight, but minimum rates of mortality, as detailed in the following Table 2.

TABLE 2

SICKLEPOD DRY WEIGHT AND MORTALITY AS AFFECTED BY RINSING OF *MYROTHECIUM VERRUCARIA* CONIDIA

| TREATMENT[1] | DRY WEIGHT (g) | DRY-WEIGHT REDUCTION (%) | MORTALITY (%) |
| --- | --- | --- | --- |
| Control[2] | 3.7 | 0.0 | 0.0 |
| $4 \times 10^7$ Conidia Per Milliliter[3] | 0.3 | 92.6 | 83.3 |
| $4 \times 10^7$ Conidia Per Milliliter (Rinsed)[4] | 3.9 | −5.5 | 0.0 |
| Cell-Free Filtrate[5] | 0.5 | 86.1 | 2.8 |

[1]Sicklepod plants in the cotyledonary to first-true leaf stage of growth were sprayed to wetness with each treatment. The plants were placed in a dew chamber at 25 C for 6 hours, then moved to a greenhouse bench. Plants were excised at the soil line 14 days after inoculation and dried 7 days at 75 C. Data are averages of three replications, 12 plants each.
[2]Silwet L-77 surfactant (0.5%).
[3]Conidia were harvested in .05% surfactant by rinsing cultures grown on potato dextrose agar.
[4]Rinsed in distilled water by three centrifugation cycles at 840 × g for 10 minutes. After the third centifugation cycle, the conidia were resuspended in .05% surfactant.
[5]Supernatant from first centrifugation cycle of a suspension containing $4 \times 10^7$ conidia per milliliter in .05% surfactant was filtered through 0.2μ membrane filters.

EXAMPLE 9
Combination of *M. verrucaria* and *Alternaria cassiae* for Control of Sicklepod

*Alternaria cassiae* Juriar and Khan has been studied as a potential biological control agent for sicklepod. Studies were conducted to determine if sicklepod control could enhanced by combinations of *A. cassiae* and *M. verrucaria*.

Sicklepod plants in the cotyledon to first leaf growth stage were inoculated with concentrations of various combinations of *A. cassiae* and *M. verrucaria* conidia that typically produce mortality rates of 50% or less, as detailed in the following Table 3.

TABLE 3

SICKLEPOD MORTALITY AS AFFECTED BY COMBINATIONS OF *MYROTHECIUM VERRUCARIA* AND *ALTERNARIA CASSIAE*

| TREATMENT[1] | MORTALITY (%) |
| --- | --- |
| Control[2] | 0.0 |
| *M. verrucaria*[3] | 0.0 |
| *M. verrucaria* (rinsed spores)[4] | 0.0 |
| Filtrate[5] | 0.0 |
| *M. verrucaria* (rinsed spores) + Filtrate[6] | 0.0 |
| *A. cassiae*[7] | 33.0 |
| *A. cassiae* + *M. verrucaria*[8] | 81.0 |
| *A. cassiae* + Filtrate[9] | 81.0 |

[1]Sicklepod plants in the cotyledonary to first true-leaf stage of growth were sprayed to wetness with each treatment. The plants were placed in a dew chamber at 25 C for 6 hours, then moved to a greenhouse bench. Data, collected 14 days after treatment, are averages of three replications, 12 plants each.
[2]Silwet L-77 surfactant (0.05%).
[3]Inoculum contained $1 \times 10^7$ conidia per milliliter in surfactant (0.05%).

TABLE 3-continued

SICKLEPOD MORTALITY AS AFFECTED BY COMBINATIONS OF
MYROTHECIUM VERRUCARIA AND ALTERNARIA CASSIAE

| TREATMENT[1] | MORTALITY (%) |
| --- | --- |

[4]Conidia were harvested from cultures grown on potato dextrose agar by rinsing with 0.05% surfactant. These conidia were rinsed three times in distilled water by sequential centrifugation cycles at 840 × g for 10 minutes. After the third centrifugation cycle, the conidia were resuspended in 0.05% surfactant.
[5]A cell-free filtrate was prepared by filtering the supernatant from the first centrifugation cycle through 0.2μ membrane filters.
[6]Pellets of rinsed conidia from the third centrifugation cycle were resuspended in cell-free filtrate so that the concentration of conidia was 1 × 10[7] conidia per milliliter.
[7]Alternaria cassiae inoculum contained 5 × 10[4] conidia per milliliter in 0.05% surfactant.
[8]Alternaria cassiae inoculum (5 × 10[4]) plus Myrothecium verrucaria inoculum (1 × 10[7]) (unrinsed).
[9]Alternaria cassiae inoculum (5 × 10[4] per milliliter) suspended in cell-free filtrate prepared from Myrothecium verrucaria conidia.

Results recorded after 14 days indicate rates of mortality when the two pathogens were combined that exceeded the additive effects of the pathogens (Table 3).

Combinations of A. cassiae and M. verrucaria exhibited synergistic activity that could not have been predicted. Many organisms used in combination exhibit antagonistic activity toward each other. Results indicating that A. cassiae and M. verrucaria can be used in combination could not have been predicted. This is especially true in view of our observations and reports by others that M. verrucaria inhibits the growth of a number of fungi, including Alternaria spp.

The experimental parameters used in examples cited for this invention are not intended to limit the scope of this invention. Modification of factors such as inoculum concentrations, parameters for inoculum production, surfactants, application methods, and other factors, would be expected to influence efficacy of this invention. Parameters were selected to enable detection of interactions, to document the relationship of this invention to the prior art, and to illustrate that the unique and surprising characteristics of this invention were not obvious and could not have been predicted from the prior art.

While we recognize that various plant species will exhibit some differences in response to this pathogen, the scope of this invention relates to the use of M. verrucaria as a broad-spectrum biological herbicide. As indicated in Table I, sicklepod is only one example of numerous weed species that are affected by M. verrucaria. Examples utilizing sicklepod as the target species are not intended to limit the scope of this invention.

While the preferred embodiments have been described above, it will be recognized and understood that various modifications may be made in the invention and the appended claims are intended to cover all such modifications which may fall within the spirit and scope of the invention.

Having described my invention with the particularity set forth above, what is claimed is:

1. A method for the biological control of weeds, comprising the steps of culturing a herbicidal effective amount of conidia of the fungus Myrothecium verrucaria (Alb. and Schwein.) Ditmar ex Fr. on a suitable growth medium; harvesting said conidia; and inoculating the weeds with a herbicidal effective amount of said conidia of the fungus Myrothecium verrucaria (Alb. and Schwein.) Ditmar ex Fr., wherein said weeds are inoculated with said conidia by applying said conidia to said weeds in a liquid surfactant.

2. The method of claim 1 wherein said weeds are inoculated with a mixture of conidia of the fungus Myrothecium verrucaria (Alb. and Schwein.) Ditmar ex Fr. and conidia of the fungus Alternaria cassiae (Juriar and Khan) in a liquid surfactant.

3. The method of claim 1 wherein said surfactant is selected from the group consisting of a silicone-polyether copolymer spray adjuvant, oxysorbic (20 POE) (polyoxyethylene sorbitan mono oleate) and nonoxynol (9 to 10 POE) (α-[p-nonylphenyl-ω-hydroxypoly (oxyethylene)]).

4. A method for the biological control of a variety of weeds, comprising the steps of culturing a herbicidal effective amount of conidia of the fungus Myrothecium verrucaria (Alb. and Schwein.) Ditmar ex Fr. on a suitable growth medium; harvesting said conidia; rinsing said conidia with a liquid surfactant; and inoculating the weeds with a mixture of said liquid surfactant and said conidia.

5. The method of claim 4 further comprising the step of mixing the fungus Alternaria cassiae (Juriar and Khan) with the fungus Myrothecium verrucaria (Alb. and Schwein.) Ditmar ex Fr. prior to said inoculating of the weeds.

6. The method of claim 4, wherein said surfactant is selected from the group consisting of a silicone-polyether copolymer spray adjuvant, oxysorbic (20 POE) polyoxyethylene sorbitan mono oleate and nonoxynol (9 to 10 POE) [α-(p-nonylphenyl)-ω-hydroxypoly (oxyethylene)].

7. A method for the biological control of weeds growing with crop plants, comprising the steps of inoculating the weeds with a herbicidal effective amount of conidia of the fungus Myrothecium verrucaria (Alb. and Schwein.) Ditmar ex Fr. in a liquid surfactant and applying said conidia of the fungus and said liquid surfactant to the weeds beneath the canopy of the crop plants.

8. The method of claim 7 wherein said surfactant is selected from the group consisting of a silicone-polyether copolymer spray adjuvant, oxysorbic (20 POE) (polyoxyethylene sorbitan mono oleate) and nonoxynol (9 to 10 POE) (α-[p-nonylphenyl-ω-hydroxypoly (oxyethylene)]).

9. A method for the biological control of sicklepod comprising the step of inoculating the sicklepod with a herbicidal effective amount of the fungus Myrothecium verrucaria (Alb. and Schwein.) Ditmar ex Fr. in a liquid surfactant.

10. The method of claim 9 wherein said sicklepod is inoculated with a mixture of the fungus Myrothecium verrucaria (Alb. and Schwein.) Ditmar ex Fr. and the fungus Alternaria cassiao (Juriar and Khan) in a liquid surfactant.

11. The method of claim 9 wherein said surfactant is selected from the group consisting of a silicone-polyether copolymer spray adjuvant, oxysorbic (20 POE) (polyoxyethylene sorbitan mono oleate) and nonoxynol (9 to 10 POE) (α-[p-nonylphenyl-ω-hydroxypoly (oxyethylene)]).

* * * * *

UNITED STATES PATENT AND TRADEMARK OFFICE
CERTIFICATE OF CORRECTION

PATENT NO. : 5,747,029
DATED : May 5, 1998
INVENTOR(S) : Harrell L. Walker et al.

It is certified that error appears in the above-indentified patent and that said Letters Patent is hereby corrected as shown below:

Column 5, line 4, change "NH4" to -- $NH_4$ --.
Column 6, line 11, change "840x g" to -- 840 x g --.
Column 10, line 65, change "$20x10^5$" to -- $20x10^6$ --.

Signed and Sealed this

Fourth Day of August, 1998

*Attest:*

BRUCE LEHMAN

*Attesting Officer*     Commissioner of Patents and Trademarks